US005380279A

United States Patent [19]

Schmidt

[11] Patent Number: 5,380,279
[45] Date of Patent: Jan. 10, 1995

[54] ANIMAL VACCINATION GUN

[75] Inventor: Conrad Schmidt, Nobles County, Minn.

[73] Assignee: The Upjohn Company, Kalamazoo, Mich.

[21] Appl. No.: 209,803

[22] Filed: Mar. 11, 1994

[51] Int. Cl.[6] ............ A61B 17/20
[52] U.S. Cl. ............ 604/46; 604/131; 604/143
[58] Field of Search ............ 604/46, 131, 134, 135, 604/143, 146, 147, 218, 140, 141

[56] References Cited

U.S. PATENT DOCUMENTS 3,086,530 4/1963 Groom ............ 604/46 X
3,474,787 4/1968 Grant .
4,186,741 2/1980 Cesaro .
4,301,795 11/1981 Zimmerman ............ 604/143
4,384,579 5/1983 Lucas .
5,015,237 5/1991 Kleinwolterink, Jr. et al. ... 604/141 X
5,176,645 1/1993 Guerrero ............ 604/143

*Primary Examiner*—John D. Yasko
*Attorney, Agent, or Firm*—Flynn, Thiel, Boutell & Tanis

[57] ABSTRACT

An animal vaccination gun for administering a vaccination to an animal has a movable needle assembly which is brought into engagement with a metering chamber having a spring-biased piston mounted therein during the injection of a medicament to an animal. During the injection, fluid is forced out of the metering chamber and through the needle assembly by the spring-biased piston. After the injection, fluid pressure forces the needle assembly out of engagement with the metering chamber and enables the metering chamber to be refilled.

7 Claims, 10 Drawing Sheets

ANIMAL VACCINATION GUN

FIELD OF THE INVENTION

This invention relates to the vaccination of animals and, more particularly, to an apparatus for vaccinating animals by means of an animal vaccination gun. The animal vaccination gun is capable of accurately effecting multiple deliveries of a predetermined amount of a vaccine without refilling.

DESCRIPTION OF THE PRIOR ART

Animal vaccination guns currently in use typically depend on energy from the hand and arm muscles of the user to force a vaccine through a hypodermic needle into an animal to be inoculated. These typical prior art vaccination guns typically comprise a spring-loaded plunger mounted in a syringe bore which fills with a medicament as the plunger is retracted along the bore and compresses the spring. After the plunger has been retracted to a desired position, it is held in this position and, when it is desired to administer the medicament, a trigger mechanism is activated which releases the plunger and allows the spring to decompress and force the medicament out of the syringe bore and into the animal. These prior art vaccination guns have problems in that it typically requires that the operator use both hands during the vaccination procedure, a great deal of operator energy is expended during the vaccination of large numbers of animals, the process of vaccinating an animal takes an undesirable amount of time and it is difficult to assure that a uniform amount of medicament is administered during each inoculation.

Grant U.S. Pat. No. 3,474,787, Cesaro U.S. Pat. No. 4,186,741 and Lucas U.S. Pat. No. 4,384,579 all disclose typical prior art injection devices which use spring driven plungers to force a medicament out of a syringe bore in order to inoculate a subject. However, all of the hypodermic devices disclosed in these references have the same problems as discussed above and are also not capable of effecting multiple deliveries of a vaccine without being reloaded.

Accordingly, it is an object of the present invention to provide an improved animal vaccination gun which can be used in the vaccination of animals without the attendant problems associated with the prior art vaccination devices.

It is a further object of the present invention to provide an animal vaccination gun which enables the vaccination of a large amount of animals in a short period of time with relative operator ease.

It is a further object of the present invention to provide an animal vaccination gun which is capable of accurately administering multiple doses of a medicament without having to be reloaded.

SUMMARY OF THE INVENTION

These and other objects of the present invention are accomplished by providing an animal vaccination gun comprising a housing having a fluid inlet means provided at one end thereof and a fluid outlet means provided at a second end thereof. The housing contains at least one chamber with a spring-biased piston slidably mounted therein. The fluid discharge means comprises a needle mounted on a spool valve which is slidably mounted in the housing between an extended position and a retracted position which brings the needle in fluid communication with the chamber. When the needle is brought into fluid communication with the chamber, the spring-loaded plunger delivers a controlled amount of medicament out of the chamber, through the needle and into an animal to be inoculated. A check valve is provided in the fluid inlet means to prevent the medicament from being expelled thereout during the delivery of the medicament. The filling of the fluid chamber can be accomplished by either another fluid chamber having a spring-loaded plunger mounted therein or by an air compressible bladder which contains the medicament and is in fluid communication with the delivery chamber.

DETAILED DESCRIPTION OF THE PREFERRED EMBODIMENTS

Figure 1:
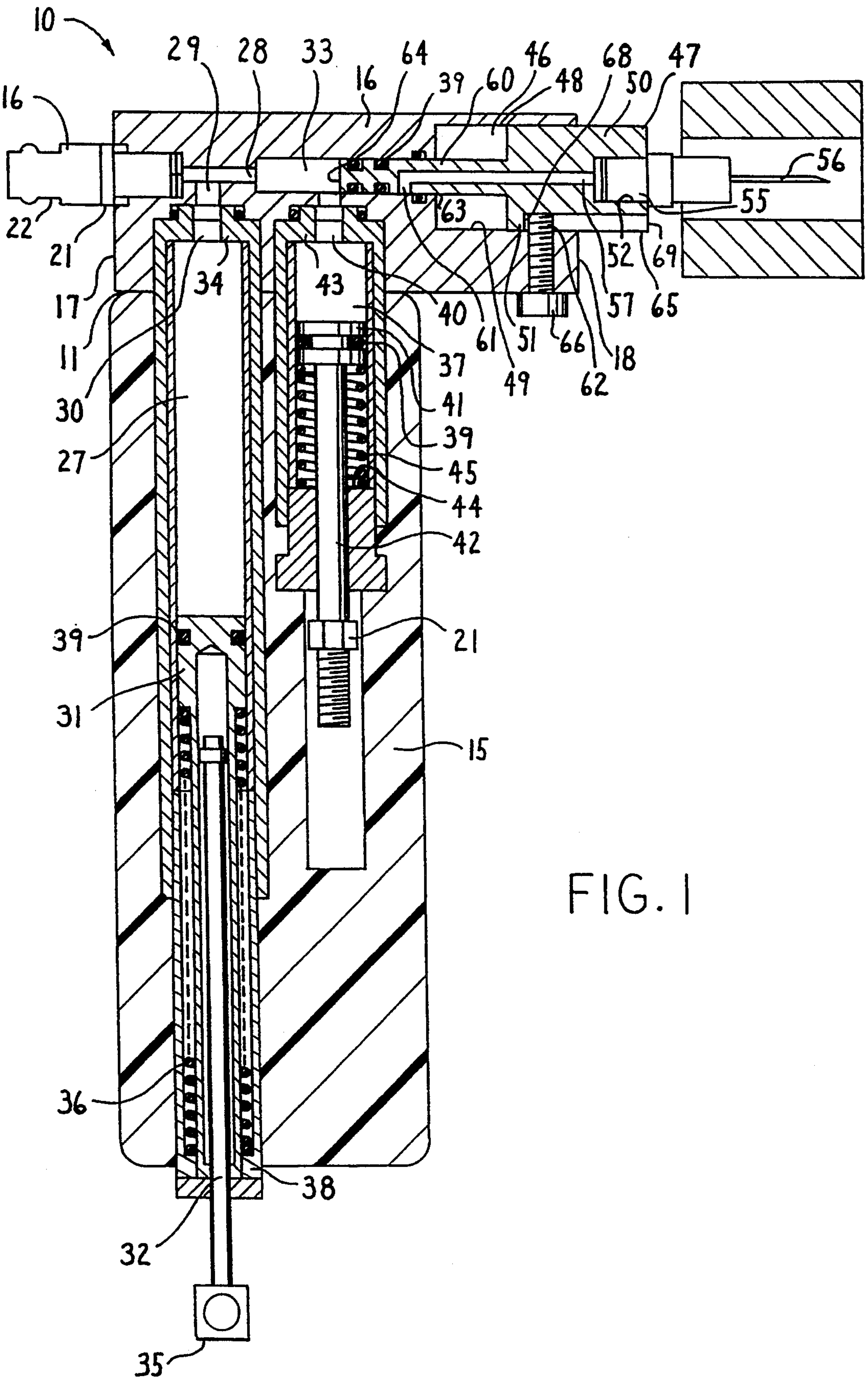
FIG. 1 is a partial sectional view of an animal vaccination gun according to a first embodiment of the present invention.

Referring to FIGS. 1–5, an animal vaccination gun 10, according to a first embodiment of the present invention, comprises a housing 11 made up of an upper box-shaped housing portion 12 and a lower pistol griplike handle housing portion 15. The housing upper portion 12 is defined by top, bottom, side, front and back walls and has a fluid inlet means 16 provided in the back wall 17. The fluid inlet means 16 comprises a one-way valve 20 made up of a valve base 21 directly inserted in back wall 17 and a valve top 22 engaged with the valve base 21. The valve top 22 has its outer surface shaped in the form of a nipple in order to aid in the attachment of a hose thereto. The one-way valve 16 has an inner flow passage 25 which communicates with a flow passage 28 provided in the upper housing portion 12 and extends throughout the length of the valve 20 and a plug 26 positioned in the flow passage 25 such that a fluid is allowed to enter the housing 11 through the one-way valve 20 but cannot exit from said housing 11 through the one-way valve 20.

The housing flow passage 28 comprises a narrow first portion 29 and a wide second portion 33 and extends laterally throughout the housing 11. The housing flow passage first portion 29 is in fluid communication with a filling chamber 27 through an opening 30 provided in a top wall 34 thereof. The filling chamber 27 has top, bottom and sidewalls defining an enclosure with the opening 30 in the top wall 34 and which extends along the length of the lower housing portion 15.

A piston 31 is slidably mounted in the filling chamber 27 for movement along the length thereof. The sides of the piston 31 are in sealing relationship with the sidewalls of the filling chamber 27 such that the movement of the piston 31 along the length of the chamber 27 effectively determines the volume thereof. An elongated rod 32 is affixed to the bottom side of the piston 31 and extends through the bottom wall 38 of the filling chamber 27 and outside of the housing lower portion 15. A handle 10 is attached to the bottom of the elongated rod 32 in order to enable the operator to control the movement of the piston 31 in the filling chamber 27. A compressible spring 36 surrounds the elongated rod 32 and is confined between the bottom surface of the piston 31 and the bottom wall 38 of the filling chamber 27 and biases the piston 31 upwardly toward the opening 30.

The second portion 33 of the housing flow passage 28 communicates with a metering chamber 37 provided in the housing 11 through an opening 40 provided in the top wall 43 of the metering chamber 37. The metering chamber 37 comprises top wall 43, bottom wall 44 and sidewalls which define an enclosure which extends along the length of the lower housing portion 15 and communicates with the second portion of the housing flow passage through the opening 40 in the top wall 43. A second piston 41 is slidably mounted in the metering chamber 37 for movement along the length thereof. The sides of the second piston 41 are similarly engaged with the sidewalls of the metering chamber 37 such that the movement of the second piston 41 along the length of the metering chamber 37 effectively determines the volume thereof. A second elongated rod 42 is attached to the underside of the second piston 41 and extends through the bottom wall 44 of the metering chamber 17. A second spring 45 surrounds the second elongated rod 42 and is confined between the bottom wall 44 of the metering chamber 37 and the bottom surface of the second piston 41. The spring 45 biases the second piston 41 upwardly towards the opening 40.

A large bore 46 is formed in the front wall 18 of the housing upper portion 12 and is in communication with the housing flow passage second portion 33. A spool valve 47 is slidably mounted for movement in the large bore 46. The spool valve 47 has a first portion 50 with a top wall in sealing engagement with the upper wall 48 of the bore 46 and a bottom wall having a lip 51 in sealing engagement with a bottom wall 49 of the bore 46. An outer portion of the spool valve first portion extends outwardly of the housing upper portion 12 and has an opening 52 provided therein for receiving a coupling member 55 for attaching a hypodermic needle 56. A fluid passage 57 extends horizontally through the spool valve first portion 50 from the opening 52 and into a spool valve second portion 60 which is slidably positioned in the housing flow passage second portion 33. The spool valve second portion is defined by a back, top, bottom and sidewalls with the top, bottom and sidewalls being in sealing relationship with the housing flow passage second portion 33. An opening 61 is provided in the bottom wall 63 of the spool valve second portion 60 and extends upwardly in the spool valve second portion to communicate with the fluid passage 57. The opening 61 is located in the bottom wall 63 of the spool valve second portion 60 at a position such that movement of the spool valve first portion 50 into the bore 46 brings the opening 61 into fluid communication with the metering chamber opening 40 so that the contents of the metering chamber 37 can be discharged through the fluid passage 57 and out of the needle 56.

In order to prevent the movement of the spool valve 47 when the animal vaccination gun 10 is not being used, a locking mechanism 62 can be provided. Locking mechanism 62 comprises a rectangular shaped member having a top, bottom, front, rear and sidewalls. The back wall 68 of the rectangular member abuts against the lip 51 and the rectangular member front wall 69 extends from the upper housing 12 at least as far as the spool valve first portion 50. The rectangular member 65 has an opening provided therein which is aligned with an opening provided in a lower part of the upper housing and both openings are adapted to receive a pin or screw 66 which maintains the rectangular member 65 in position between the housing upper portion 12 and the spool valve 47 and prevents the spool valve 47 from being moved.

All of the moving members of the present invention are provided with O-ring seals 39 made of a suitable material, such as Viton® (a copolymer of vinylidene fluoride and hexafluoropropylene), in order to prevent leakage. The material of construction of the animal vaccination gun 10 is not critical and can be of any material which is inert and will not contaminate the medicament in the environment of use. For instance, the filling chamber 27 and the metering chamber 37 can be made of glass, an inert plastic or any other suitable material and the housing 11 can be made of a light weight, high strength material such as an engineering plastic.

Figure 6:
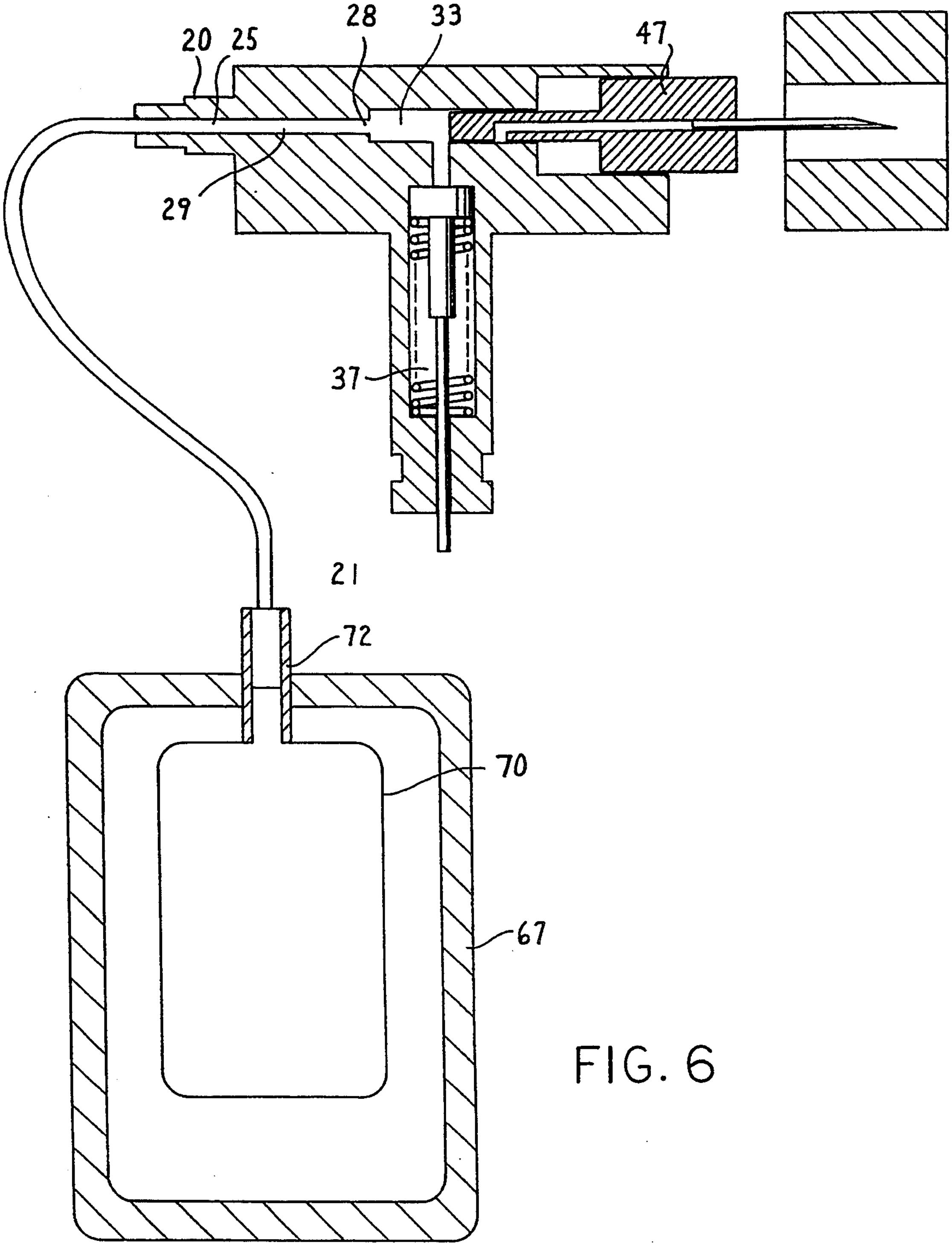
FIG. 6 illustrates the operation of an animal vaccination gun according to a second embodiment of the present invention during the filling of the metering chamber.

A second embodiment of the present invention is illustrated in FIG. 6. This embodiment is identical to the first embodiment with the exception that the filling chamber 27 and its associated members are eliminated and replaced by a compressed air tank 67 provided with a bladder of fluid 70 contained therein. A hose 71 couples the outlet 72 of the bladder to the one-way valve 20. The one-way valve 20 has a flow passage 25 which is in flow communication with a flow passage 28 which extends horizontally through the housing. The flow passage 28 is made up of a first narrow portion 29 and a second wider portion 33. The second portion of the housing flow passage 33 is in fluid communication with a metering chamber 37 in the same manner as in the first embodiment. The remaining features of the second embodiment of the present invention are identical to those of the first embodiment.

OPERATION

Figure 2:
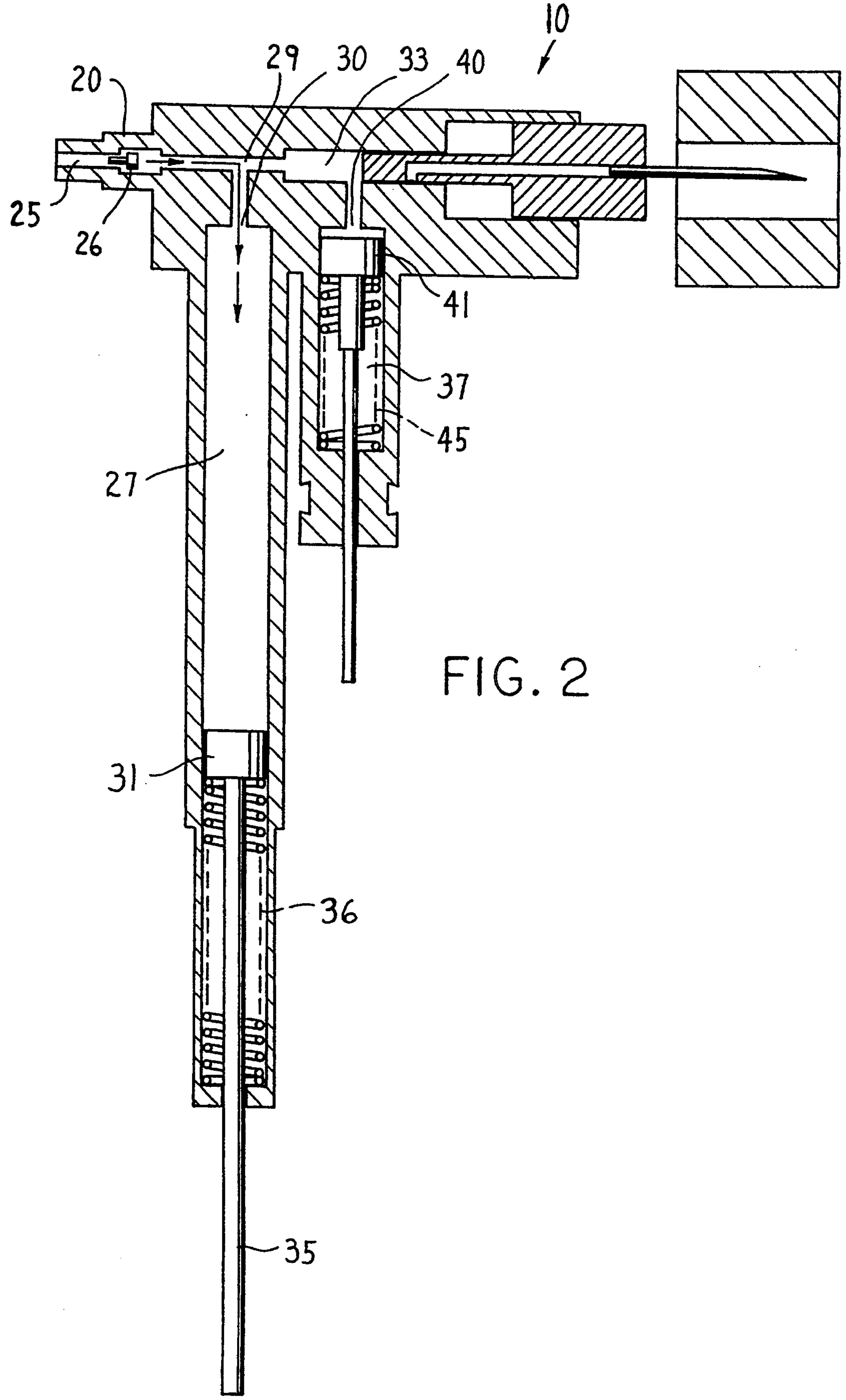
FIG. 2 illustrates the operation of an animal vaccination gun according to the first embodiment of the present invention during the filling of a first fluid chamber.
Figure 3:
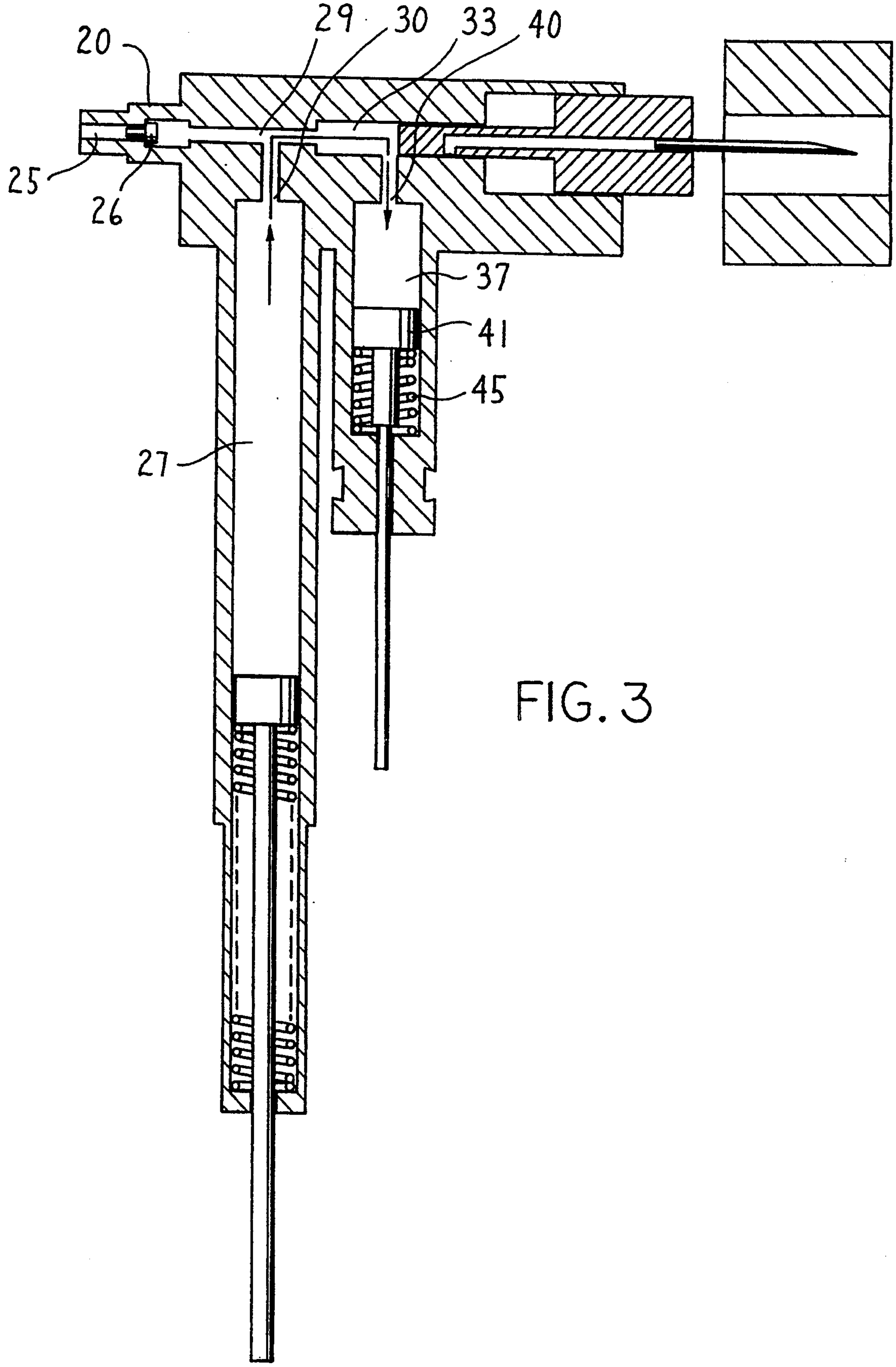
FIG. 3 illustrates the operation of an animal vaccination gun of a first embodiment of the present invention during the filling of the metering chamber.

The operation of the first embodiment of the present invention will be described with reference to FIGS. 2–5. As shown in FIG. 2, the animal vaccination gun 10 is connected to a source of a medicament (not shown) by a hose (not shown) attached to the one-way valve 20. The medicament is introduced into the filling chamber 27 by pulling the piston 31 down in the filling chamber 27 against the bias of the spring 36 by pulling the handle 35 down. The moving of the piston 31 downwardly in the filling chamber 27 creates a vacuum and induces the medicament to enter into the filling chamber 27 via the valve flow passage 25 and the housing flow passage first portion 29. After the desired amount of medicament has entered into the filling chamber 27, the handle 35 is released which allows the spring 36 to displace the piston 31 upwardly and thereby force the fluid to flow out of the filling chamber opening 30. The fluid flows out of the filling chamber 27 and into the housing flow passage first portion 29 and forces the plug 26 to close the valve flow passage 25 to prevent the fluid from flowing out of the one-way valve 20.

Since the fluid cannot flow out of the one-way valve 20, the spring biased piston 31 forces it to flow into the housing flow passage second portion 33 and into the metering chamber 37 via the metering chamber opening 40. Since the bias of the spring 36 in the filling chamber 27 is stronger than the bias of the spring 45 in the metering chamber 37, the piston 41 in the metering chamber is forced downwardly against the bias of the spring 45 by the fluid filling the metering chamber 37. As the first piston 31 delivers fluid from the filling chamber 27 into the metering chamber 37, the spring 36 causes it to retract slightly into the filling chamber 27. After the fluid has been introduced into the metering chamber 37, the animal vaccination gun 10 is then ready to administer an injection of the medicament.

Figure 4:
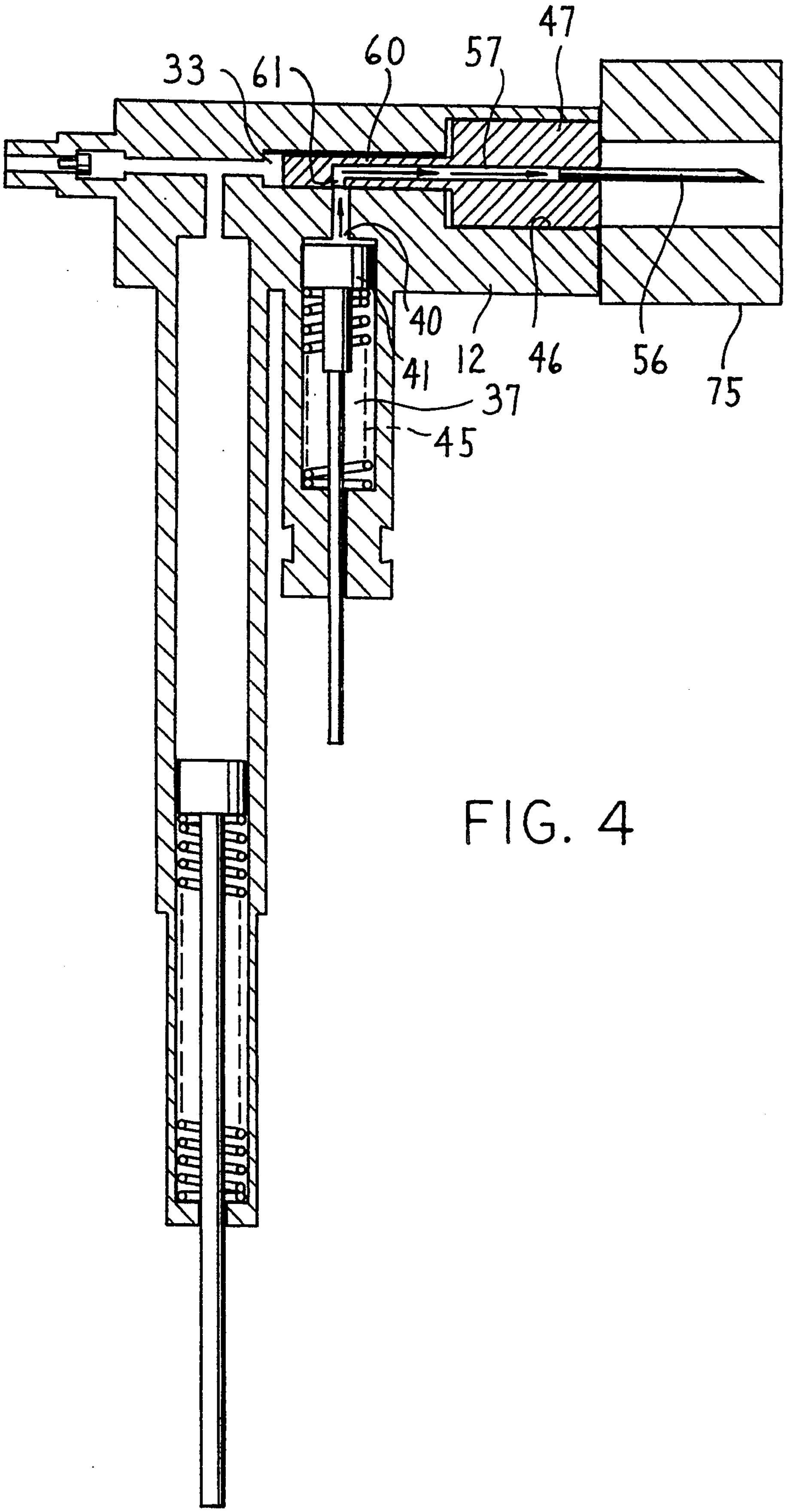
FIG. 4 illustrates the operation of an animal vaccination gun according to the first embodiment of the present invention during the discharging of a medicament from the metering chamber through a needle.

As shown in FIG. 4, in order to administer an injection of the medicament, the needle 56 is inserted into the skin 75 of the animal to be vaccinated and the spool valve 47 forced back into the housing upper portion 12 by contact of the spool valve 47 with the animal's skin 75. The spool valve 47 slides back into the housing bore 46 in the housing flow passage second portion 33 until the opening 61 provided in the spool valve second portion 60 is brought into fluid communication with the opening 40 of the metering chamber 37. Due to the bias of the spring 45, the piston 41 in the metering chamber 37 is forced upwardly thereby expelling the fluid from the metering chamber through the fluid passage 57 provided in the spool valve 47, out of the needle 56 and into the animal.

Figure 5:
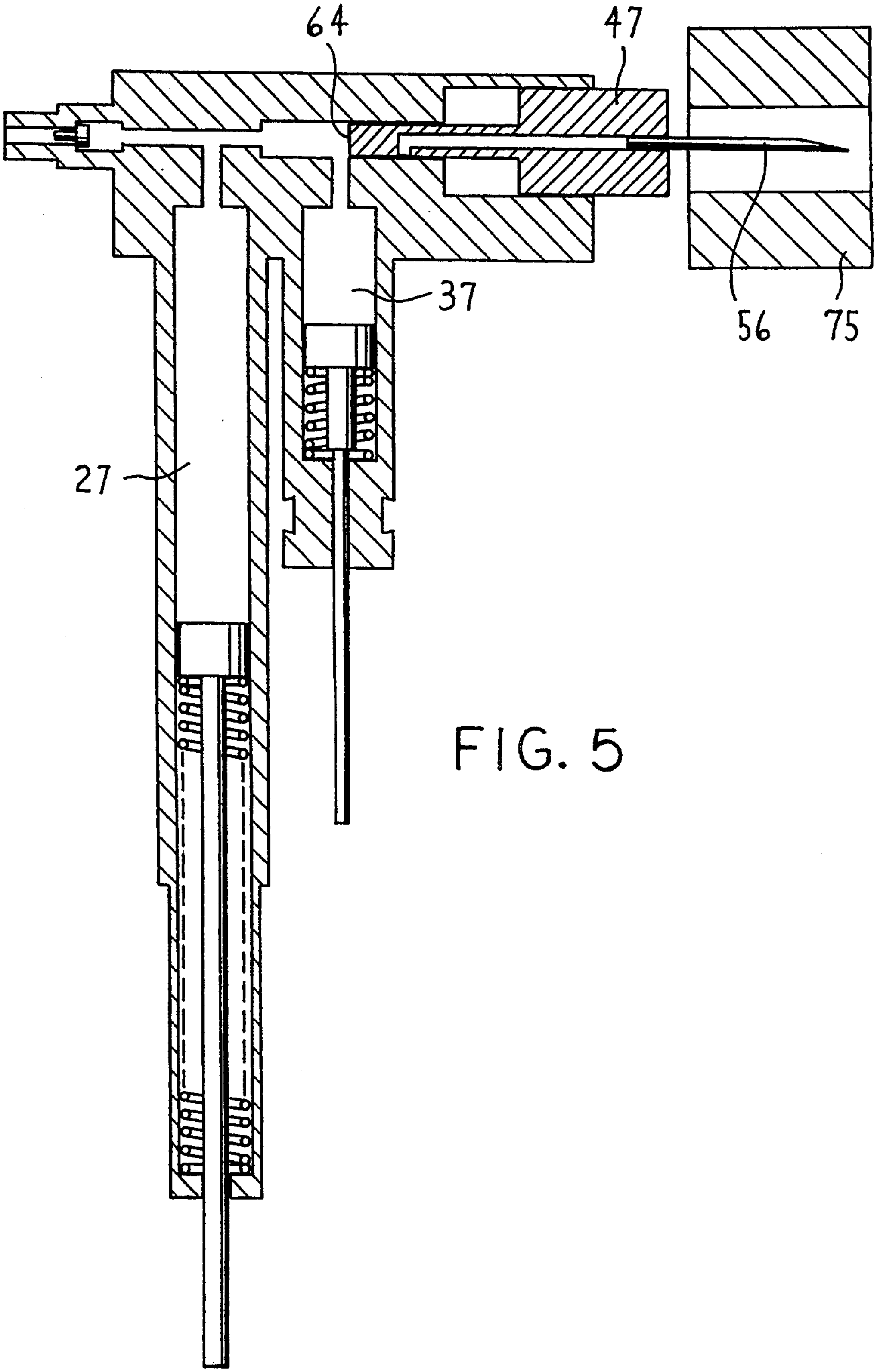
FIG. 5 illustrates the operation of an animal vaccination gun according to the first embodiment of the present invention during the automatic refilling of the metering chamber after an injection.

As shown in FIG. 5, when the needle 56 is removed from the skin 75 of the animal, the fluid pressure from the filling chamber 27 against the back wall 64 of the spool valve second portion 60 forces the spool valve 47 to return to its normal extended position. The movement of the spool valve 47 to its normal position allows the filling chamber 27 to once again enter into fluid communication with the metering chamber 37 and thereby introduce another dosage of medicament therein. This operation can be repeated until all of the medicament in the filling chamber has been expelled.

Figure 7:
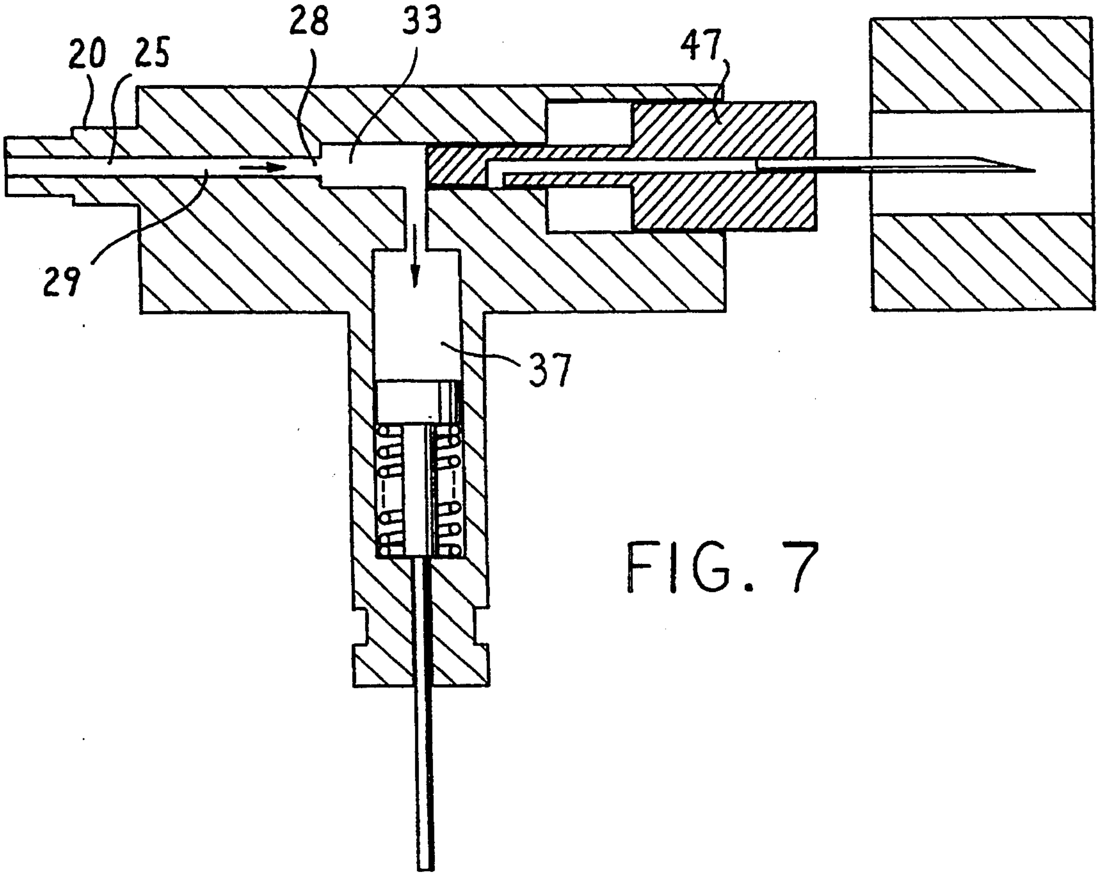
FIG. 7 illustrates the operation of an animal vaccination gun according to a second embodiment of the present invention in which the metering chamber is full.
Figure 8:
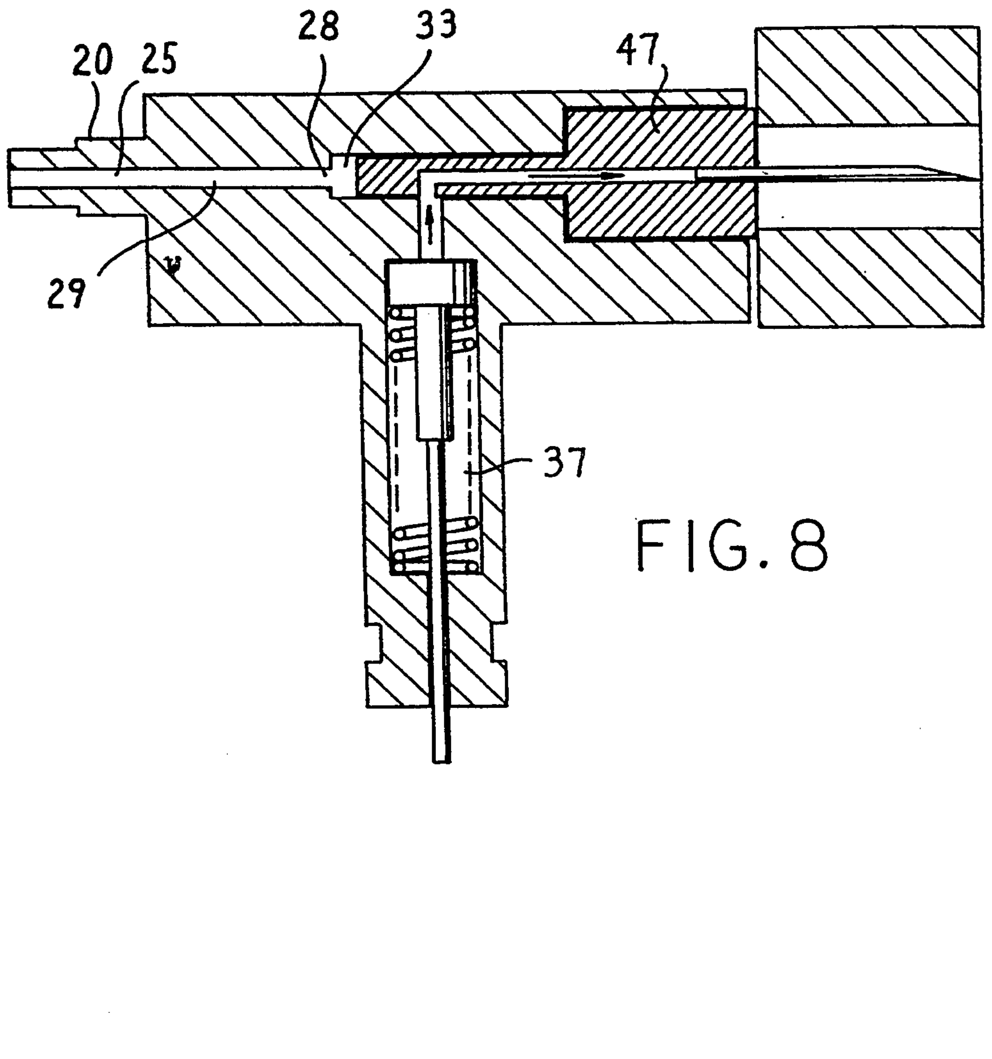
FIG. 8 illustrates the operation of an animal vaccination gun according to a second embodiment of the present invention in which the medicament is discharged out of the metering chamber and through a needle during the injection of the needle.
Figure 9:
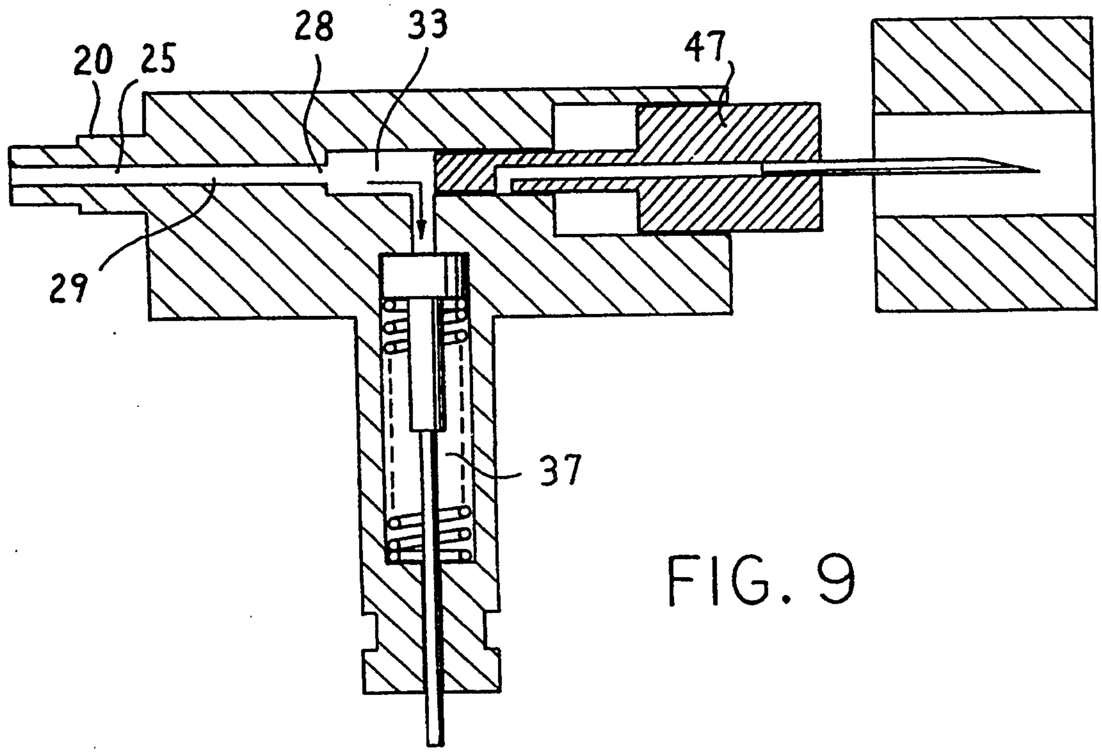
FIG. 9 illustrates the operation of an animal vaccination gun according to a second embodiment of the present invention immediately after the injection of the medicament.
Figure 10:
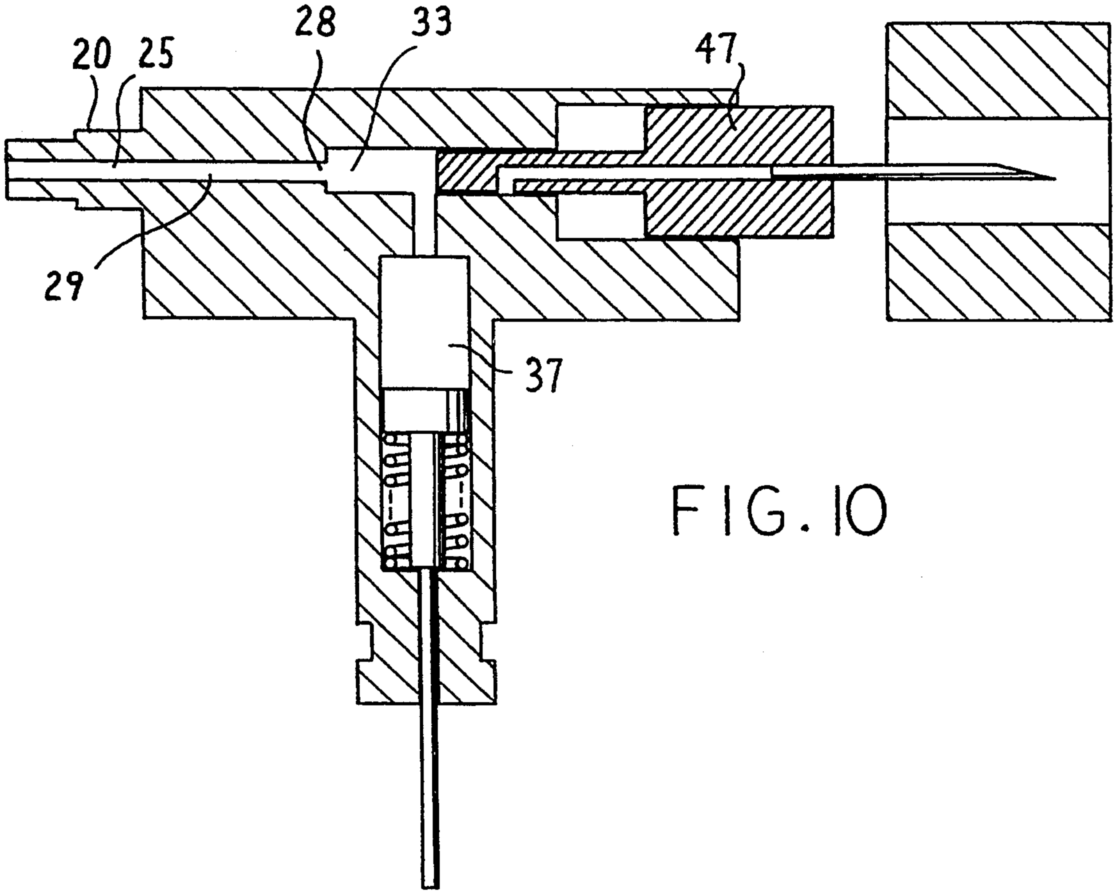
FIG. 10 illustrates the operation of an animal vaccination gun according to a second embodiment of the present invention in which the metering chamber is refilled for the next injection.

The operation of the second embodiment of the present invention is illustrated in FIGS. 6–9. The operation of this second embodiment is identical to that of the first embodiment except that a compressed air tank 67 and a bladder of fluid 70 contained in the compressed air tank 67 are used to introduce the fluid into the metering chamber 37 as opposed to the filling chamber 27 in the first embodiment. The filling of the metering chamber 37 is shown in FIG. 7 and the injection of the medicament is illustrated in FIG. 8. FIG. 9 illustrates the resetting of the spool valve 47 and the refilling of the metering chamber 37.

Although the present invention has been described with reference to particular embodiments, the invention contemplates such changes or modifications as lie within the scope of the appended claims.

The embodiments of the invention in which an exclusive property or privilege is claimed are defined as follows:

1. An animal vaccination gun comprising a housing with a fluid inlet means provided at a first end thereof and a fluid outlet means provided at a second end thereof, said fluid inlet means comprising a one-way valve for allowing fluid to be introduced into said housing and preventing fluid from exiting said housing through said fluid inlet means, a filling chamber in fluid communication with said fluid inlet means, said filling chamber having a first spring-biased piston slidably mounted therein for movement between a fully extended position and a fully retracted position, the spring biasing said first piston towards the fully extended position, a metering chamber in fluid communication with said filling chamber through a fluid conduit connecting said filling and metering chambers, said metering chamber having a second spring-biased piston slidably mounted therein for movement between a fully extended position and a fully retracted position, the spring biasing said second piston towards the fully extended position, said fluid outlet means comprising a fluid discharge member slidably mounted in said housing for movement between an extended position and a retracted position, said fluid discharge member having a first portion positioned in said fluid conduit, a second portion which extends out of said housing and has a needle provided at an end thereof and an opening provided in said first portion which is in fluid communication with said needle, said fluid discharge member first portion preventing flow between said filling chamber and said metering chamber and placing said metering chamber in fluid communication with said needle through said opening when said fluid discharge member is in the retracted position.

2. The animal vaccination gun of claim 1, additionally comprising stop means for limiting the amount the fluid discharge member extends from the housing.

3. The animal vaccination gun of claim 1, wherein said opening in said fluid discharge member first portion is sealed when said fluid discharge member is in the extended position.

4. An animal vaccination gun comprising a housing with a fluid inlet means provided at a first end thereof and a fluid outlet means provided at a second end thereof, a metering chamber in fluid communication with said fluid inlet means through a fluid conduit connecting said fluid inlet means and said metering chamber, said metering chamber having a spring-biased piston slidably mounted therein for movement therein between a fully extended position and a fully retracted position, the spring biasing said piston towards the fully extended position, said fluid outlet means comprising a fluid discharge member slidably mounted in said housing for movement between an extended position and a retracted position, said fluid discharge member having a first portion positioned in said fluid conduit, a second portion which extends out of said housing and has a needle provided at an end thereof and an opening provided in said first portion which is in fluid communication with said needle, said fluid discharge member first portion preventing flow between said fluid inlet means and said metering chamber and placing said metering chamber in flow communication with said needle through said opening when said fluid discharge member is in the retracted position.

5. The animal vaccination gun of claim 4, additionally comprising a pressurized source of fluid in fluid communication with said fluid inlet means.

6. The animal vaccination gun of claim 4, additionally comprising stop means for limiting the amount the fluid discharge member extends from the housing.

7. The animal vaccination gun of claim 4, wherein said opening in said fluid discharge member is sealed when said fluid discharge member is in the extended position.

* * * * *